United States Patent [19]
Mahajan et al.

[11] Patent Number: 5,976,806
[45] Date of Patent: Nov. 2, 1999

[54] DNA LIGASE ASSAY

[75] Inventors: Pramod B. Mahajan, Urbandale; Benjamin Bowen, Des Moines; Laura A. Tagliani, Johnston, all of Iowa

[73] Assignee: Pioneer Hi-Bred International, Inc., Des Moines, Iowa

[21] Appl. No.: 09/085,902

[22] Filed: May 27, 1998

Related U.S. Application Data

[60] Provisional application No. 60/050,700, Jun. 25, 1997.

[51] Int. Cl.$^6$ .............................. C12Q 1/68; C12Q 1/00; C12Q 1/66; C12P 19/34

[52] U.S. Cl. ................. 435/6; 435/4; 435/8; 435/91.52

[58] Field of Search ............................. 435/6, 4, 8, 91.52

[56] References Cited

PUBLICATIONS

Engler et al., "DNA Ligases," in *The Enzymes*, vol. XV Nucleic Acids Part B, third edition, Paul D. Boyer, ed., Academic Press: New York, 1982, pp. 3–29.
Barker et al., Mol. Gen. Genet. 200:458–462 (1985).
Abravaya et al., Nuc. Acid. Res. 23(4):675–682 (1995).

*Primary Examiner*—Johnny F. Railey, II
*Attorney, Agent, or Firm*—Pioneer Hi-Bred International, Inc.

[57] ABSTRACT

A quantitative and functional DNA ligase assay is disclosed. The assay involves the disruption, using restriction enzymes, of a plasmid containing a reporter gene, followed by a ligation step performed in the presence of the biological sample being assayed for DNA ligase activity. The ligation reaction products are then subjected to a coupled transcription-translation reaction, and the extent of DNA ligation is then quantified.

12 Claims, 1 Drawing Sheet

DNA LIGASE ASSAY

This application claims the benefit of Provisional Application 60/050,700 filed Jun. 25, 1997.

FIELD OF THE INVENTION

This invention relates to the field of biological assays for enzymatic activity. More particularly, the present invention relates to a quantitative and functional assay for detection of DNA ligase activity in a biological sample.

BACKGROUND

The joining, or ligation, of DNA molecules is an essential step in replication, recombination, and repair of the genetic material of all living organisms. Therefore, it is not surprising that organisms ranging from viruses to humans have evolved an enzymatic system to take care of this important metabolic reaction. This enzymatic system is designated as DNA LIGASE, EC 6.5.1.1. (1–5).

Over the past four decades, considerable attention has been devoted to the study of the biochemistry and molecular biology of DNA ligases from a variety of organisms (for reviews, see 6–10). These studies have clearly established the importance of DNA ligases in maintaining the integrity of genetic material. Recent results also indicate a correlation between lack of DNA ligase activity and certain pathological conditions in humans (11–18). Furthermore, DNA ligases have also been used as invaluable tools for advancing basic research via recombinant DNA technology (19–22). Finally, DNA ligases, in concert with the polymerase chain reaction (PCR) technology, are also being used as important diagnostic reagents (23–28).

Consequently, over the years, DNA ligases have been purified and characterized from a variety of sources (2–5). Different methods have also been developed for assaying this group of enzymes. These assay methods can be broadly divided into two groups:

I. Enzyme-intermediate Characterization:

Assays involving enzyme-intermediate characterization take advantage of the fact that the DNA ligases require ATP (for viral and eukaryotic enzymes) or NAD (for bacterial enzymes) as a cofactor. The co-factor forms an adenylylated intermediate with the enzyme. Use of radiolabeled co-factor then allows one to follow the presence of DNA ligase-like activity in crude extracts (7). Such assays can be performed relatively easily and may serve as qualitative tests to indicate the presence or absence of ligase-like polypeptides in crude extracts. However, this method has several drawbacks. First of all, it is not specific for DNA ligases only. RNA ligases (29, 30) as well as mRNA capping enzymes (31) will also form AMP-adducts, and thereby can complicate interpretation of results. Secondly, this method uses radioactivity, necessitating additional precautions and waste disposal costs. Finally, this method does not constitute a true biological assay, and therefore requires additional characterization of the substrate/product for confirmation.

II. Substrate/Product Characterization:

These assays may be further divided into two subgroups: (a) structural and (b) functional. Most of the methods published thus far involve structural characterization of the substrate and/or product (7, 26, 32). Thus, two double-stranded DNA fragments, one with a free 3'—OH group and the other with a 5'—$PO_4$ group are incubated with the enzyme under appropriate conditions. The disappearance of the substrate or appearance of the products can be detected by electrophoresis alone, or by electrophoresis in combination with autoradiography (if the substrates are radiolabeled). Another variation of this method is to measure the incorporation of $^{32}P$—$PO_4$ into the phosphatase-resistant product, thereby making quantitation easier. Although these methods are currently used routinely, they also suffer from the use of radioactivity and require additional characterization of the product to prove functionality.

Recently, use of fluorescent labels for DNA substrates has been shown to have the potential to replace use of radioactivity (27, 28), thereby reducing the health related concerns, as well as increasing sensitivity significantly. However, use of sophisticated instruments makes these methods less cost effective. Moreover, the biological function of the product needs to be established separately when these methods are used. This is routinely achieved by using a plasmid containing a selectable marker (e.g. antibiotic resistance) as a substrate for the enzymatic reaction (7). Upon ligation, the reaction product is used to transform bacteria (e.g. *E. coli*) that are grown in presence of the specific antibiotic. Only those bacteria which harbor the ligated plasmid DNA containing a functionally reconstituted antibiotic marker gene will grow, indicating successful ligation and restoration of function of the product. Hence, this assay qualifies as a functional biological assay (7). However, this biological assay for DNA ligase activity (believed to be the only such biological assay currently available) is time consuming (at least two days), laborious, and qualitative rather than quantitative. Therefore, there is a particular need for a functional, quantitative assay for DNA ligase activity. The present invention describes a functional assay that is non-radioactive, extremely sensitive, quantitative, and that can be completed within 3.5 hours. Furthermore, this assay can be applied to all types of DNA ligases.

SUMMARY

Therefore, it is an object of the present invention to provide a quantitative, functional assay for DNA ligase. The present invention therefore relates to a method for detection of DNA ligase activity in a biological sample, such samples including, for example, disrupted cells or tissues, or alternatively a cDNA library.

The method of the invention involves the disruption of a plasmid containing a reporter gene, for example the GUS gene, or the luciferase gene, or the like. The plasmid can be disrupted with one or more restriction enzymes. The disrupted plasmid is then used as a substrate for a ligation reaction carried out in the presence of the biological sample. The reaction products of the ligation reaction are then at least partially purified, and the purified products are then subjected to a coupled transcription-translation reaction. The extent of ligation is then quantified by measuring the activity of the reporter gene product produced as a result of the coupled transcription-translation reaction product.

Units; Taq =10 Units used to ligate 1 µg of pPHP6331 or pPHP6265 plasmids. The purified reaction product was suspended in 50µl TE and 2 µl (appropriately 40 ng) were used in each TnT ligase reaction. Luciferase activity was measured in triplicate.

DETAILED DESCRIPTION

The following definitions are provided in order to remove ambiguities related to the intent of the scope of the usage of certain terms in the specification and claims.

A biological sample, as used herein, means any sample which could potentially contain a functional DNA ligase or containing a gene encoding and expressing a DNA ligase. For example, and not by way of limitation, such samples could include prokaryotic or eukaryotic cells that have had their cellular integrity disrupted in such a way as to preserve enzymatic, and specifically DNA ligase, functional activity. Again solely by way of example, such cells could be bacterial or yeast cells, or plant cells in suspension, or plant callus cells, and the like. Alternatively, a biological sample would also include disrupted eukaryotic tissues, including, for example, plant leaf tissue, animal or human biopsy tissue, and the like. Or the biological sample could be a preparation of the expression products of a cDNA library, made in such a way as to insure that enzymes, specifically DNA ligase, are functional, in that they are capable of reacting with an appropriate substrate in a biologically appropriate manner.

A reporter gene sequence, as used herein, means a gene sequence that, when expressed, produces a protein product that can be detected colorometrically, fluorometrically, or as a result of a chemiluminescent reaction. For example, but not by way of limitation, such genes would include the GUS gene, the luciferase gene, the apoaquorin gene, the green fluorescent protein gene, and the like.

The present invention relates to an assay for DNA ligase activity in a biological sample. A plasmid containing an expressible reporter gene sequence is constructed using methods well known in the art. The plasmid is constructed so that it contains a promoter sequence at the 5' end of the reporter gene sequence, the promoter being capable of driving expression of the reporter gene.

Figure 1:
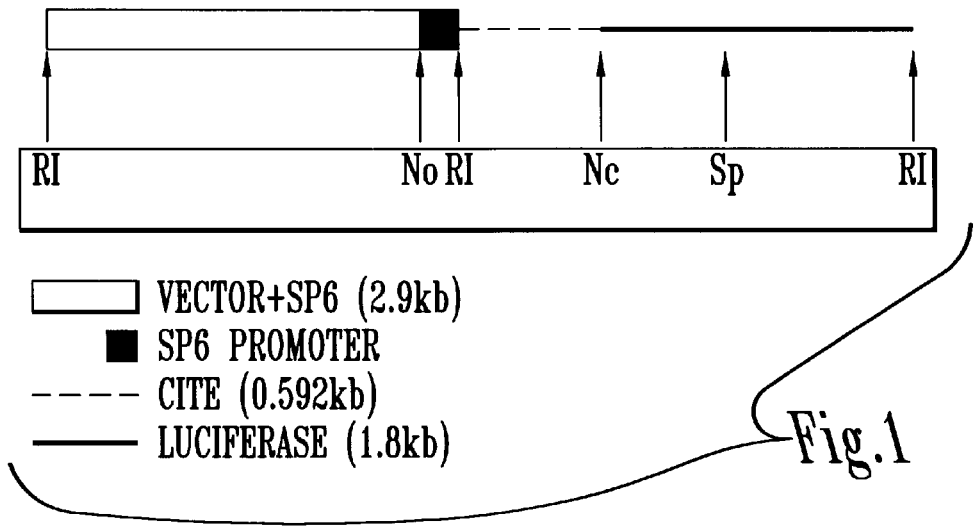
FIG. 1 is a schematic diagram showing a partial restriction map of plasmid pPHP6265. The vector sequences are represented by the open box; the solid box denotes the SP6 promoter. The broken line represents CITE sequence, and the solid line represents the luciferase coding sequence. The restriction cites are shown at the arrows, and are abbreviated as follows: RI=EcoRI; No=NotI; Nc=Ncol; Sp=SphI.

The plasmid is also constructed so that it can be disrupted by one or more restriction enzymes. In preferred embodiments of the invention, the plasmid is constructed so that it can be disrupted in such a way that the continuity of the reporter gene sequence is disrupted by the restriction enzyme treatment. In more preferred embodiments, a single restriction enzyme that truncates somewhere in the coding region of the reporter gene sequence is used. A schematic diagram showing a partial restriction map of a preferred plasmid useful in, but not necessary to, the practice of the present invention is shown in FIG. 1.

As those skilled in the art will recognize, any restriction enzyme or enzymes that will cleave or truncate at appropriate points in the reporter gene sequence and plasmid construct may be used in the practice of the invention.

Following disruption of the plasmid containing the reporter gene, a ligation reaction is performed in the presence of the biological sample, so that the biological sample serves as the only possible source of the DNA ligase, if any is present. The biological sample is prepared in any manner appropriate to the cell or tissue (or alternative) source, and in a manner such that the functional capability of any DNA ligase present in the sample is maintained.

For example, an extract of plant cell suspension cultures can be prepared as follows: Plant cell suspension cultures are harvested by filtration through cheese cloth and the wet weight of the cell pellet is noted. The cell pellet is suspended in 20 mM Hepes buffer (pH 7.9) containing 20% glycerol, 1 mM dithioerythretol, 10 mM KCl, 0.1 mM EDTA and 0.4 molar sorbitol at a ratio of 4 ml buffer per gram wet weight of cells. The suspension is mixed well and kept on ice for 10 minutes. The supernatant is removed by filtration, and the foregoing process is repeated. Finally, the cells are suspended in the same buffer as above and protease inhibitors, for example Pefabloc SC, Pepstatin and Bestatin (Boeheringer Mannheim), are added to a final concentration of 0.4 mM, 1 µM and 130 µM respectively. Cells are nebulized in the BioNebulizer (Glas-Col) four times at 100 psi. The suspension is filtered through four layers of cheese cloth. The filtrate is mixed with 0.1 vol/vol of saturated ammonium sulfate solution (pH 7.9) and stirred gently for one hour. The mixture is centrifuged at 100,000×g for 90 min. To the supernatant, solid ammonium sulfate (0.4 g /ml) is added slowly. The mixture is stirred gently for 30 minutes and centrifuged at 40,000×g for 25 minutes. The protein pellet is dissolved in minimum volume of Hepes buffer (pH 7.9) containing 20% glycerol, 100 mM KCl, 0.1 mM EDTA and 1 mM DTT, and dialyzed overnight against the same buffer. The dialysate is centrifuged at 10,000 rpm for 10 minutes to remove the insoluble material and the supernatant is used in the ligase assays. With only slight modification the foregoing protocol is also useful for making extracts from plant callus or microspore preparations.

A biological sample containing *E.coli* proteins can be prepared by following essentially the same protocol as above, except that the *E.coli* cells are grown overnight in LB medium (20) and harvested by centrifugation at 5,000 rpm for 10 minutes.

A biological sample containing the expression products of a cDNA library can be prepared by using an automated colony picker that will pick bacterial colonies from agar plates and transfer the bacteria to a 96-well microtiter plate. LB medium is added to each well and bacteria are allowed to grow overnight at 37° C. The bacterial cells are pelleted by centrifugation at 5,000 rpm for 10 minutes and pellets washed with 20 mM Hepes buffer (pH 7.9) containing 20% glycerol, 100 mM KCl, 0.1 mM EDTA and 1 mM DTT. The physical integrity of the cell is disrupted, and the resultant mixture is centrifuged at 5,000 rpm. The supernatant is used for ligase assays.

Of course, as those of skill in the art will recognize, the efficiency of the assay and the quality of the results will vary depending upon the purity of the extract and the level of nuclease activity present in the extract. In a preferred embodiment of the present invention, the biological sample is treated in order to decrease the activity of nucleases in the sample. This treatment can be a partial purification of the biological sample, prior to the ligation reaction, by ion exchange chromatographic methods using MonoS and MonoQ (Pharmacia Biotech). Alternatively, chemical treatment of the sample, for example by altering the pH or the ionic composition of the sample buffer, could be used. As an additional alternative, a chemical nuclease inhibitor could be used.

Furthermore, as those of skill in the art will recognize, the ligation reaction conditions may also vary depending upon the source of the biological sample. It would be expected that ligases from different sources could have some variation in activity profiles, and some routine optimization of reaction conditions, well within the ordinary level of skill in the art, could be expected.

Following a partial purification of the ligase reaction products (using, for example, a QIA Quick™ Purification Kit (Qiagen, Inc., U.S.A.), the ligase reaction products are subjected to a coupled transcription-translation reaction. Various methods are known to those of skill in the art that are useful in carrying out such coupled reactions. For example, kits are commercially available (including, for example, the Single Tube Protein (STP) kit from Novagen, and the TnT kit from Promega), and Drosophila, yeast, and HeLa cell systems are also known in the art. Those of skill in the art will recognize that it will be preferable to choose a promoter for use in the plasmid described above that corresponds to the polymerase used in the coupled transcription-translation reaction.

The quantitation and functional determination is accomplished by measuring the activity of the coupled transcription-translation reaction product. How this is done will of course depend upon the nature of the reporter gene product. If the product is a fluorophore, or is chemiluminescent, then appropriate detection and measurement apparatus and techniques are used. If the product produces a colorometric reaction, colorometric detection and measurement techniques are used. In preferred embodiments, the more sensitive fluorometric and chemiluminescent methods are used.

The following examples are presented for the purpose of illustrating specific embodiments within the scope of the present invention without limiting the scope of the invention as defined by the claims. Numerous variations will be readily apparent to those of ordinary skill in the art.

EXAMPLE 1

The following example describes the basic procedure for the enrichment method of the present invention when the biological materials are cultured suspension cells or callus.

Exponentially growing *Zea mays* suspension cells (80–100 g) were harvested by filtration and washed with cold BioNeb buffer (20 mM Hepes buffer pH 7.9, 20% glycerol, 0.4 molal sorbitol, 0.1 mM EDTA and suspended in the same buffer (4 ml/g cells) supplemented with 0.1 mM DTT and protease inhibitors Pefabloc, bestatin, pepstatin at recommended optimal concentrations. Homogenization was performed using the BioNebulizer (Glas-Col Co., Terre Haute, Ind.) at 100 psi of helium using a single pass mode. After four rounds of nebulization, the homogenate was quickly transferred to cold room and filtered through four layers of cheese cloth. Cold saturated ammonium sulfate solution (pH 7.9; 0.1 volume of the filtrate) was added slowly and the mixture stirred gently for one hour at 4° C. The mixture was centrifuged at 100,000×g for 1.5 hours and pellet discarded. Solid ammonium sulfate (0.4 g/ml) was added to the supernatant (S100), mixed for 30 minutes at 4° C. and centrifuged at 40,000×g for 30 minutes. The pellet was dissolved in minimum volume of HGED buffer (20 mM Hepes, pH 7.9, 20% glycerol, 0.1 mM EDTA) containing 100 mM KCl and dialyzed against the same buffer. After about 10 hours, the sedimented proteins were separated by centrifugation at 10,000 rpm for 10 minutes. The crude (WCE) thus isolated was stored at –80° C. or used directly for enzyme purification.

EXAMPLE 2

The following example describes the basic procedure for the enrichment method of the present invention when the biological materials are plant leaf tissues.

Corn leaves were collected from 6–9 week plants grown either in the green-house or in the field and quickly transferred to a blender pre-chilled to –20° C. All operations hereafter were performed at 4° C. or on ice unless mentioned otherwise.

Approximately 200g of leaves were processed in one batch using about 500–600 ml Bioneb buffer. Leaves were blended for 10 seconds at full speed on the high setting. This step was repeated three more times with about 2 minute interval between each 10 second burst. The homogenate was filtered through four layers of cheese cloth and the filtrate was centrifuged at 5000 rpm for 10 minutes. The pellet was washed two times with about 100 ml of Bioneb buffer and finally re-suspended in about 25 mls of the same buffer. The mixture was Bio-nebulized and processed as described above for the suspension cultures. Essentially similar protocols were followed to prepare WCE from microspores of *Zea mays* as well as *Lilium longiflorum*. Protein was determined using the Bradford methods (33).

EXAMPLE 3

The following example describes the basic procedure for carrying out the assay of the present invention. The source of the biological sample was a purified bacterial ligase from *E.coli* and *T.aquaticus* (commercially obtained from Boeheringer Mannheim and New England BioLabs, respectively).

Materials and Methods

Chemicals:

All reagents used in this study were of molecular biology grade and obtained from Sigma Chemical Co. Restriction enzymes and T4 DNA ligase were procured from Boehringer Mannheim. Bacterial DNA ligases were obtained from New England BioLabs. Vector pGEM9ZF(–) and reagents for TnT assays were purchased from Promega Corp. Vector pCITE-1 a and the reagents for the coupled transcription-translation assay were from Novagen, Inc. Plasmid DNA purification was performed using Nucleobond columns (Macherey-Nagel GmbH & Co.).

Plasmids:

Construction and preparation of plasmid DNA was done following standard protocols (19). A diagram of a partial restriction map of the plasmid pPHP6265 is shown in FIG. 1. This plasmid was constructed using a 2.9 kb EcoRI/Sacd fragment from the vector pGEM9ZF–(Promega Corp.); a 0.592 kb EcoRI/Ncol fragment from the vector pCITE-1a (Novagen, Inc.), and a 1.8 kb NcollSacl fragment from the plasmid pPHP1654 described earlier (34). The 2.9 kb fragment contains the SP6 and T7 promoter sequences flanking the multiple cloning site, pUC origin of replication, and the Amp$^+$resistance marker; the 0.592 kb fragment contains the 501 bp cap-independent transitional enhancer and the 1.8 kb fragment contains the firefly luciferase coding sequence (34). Plasmid pPHP6331, which lacks the SP6 promoter, but is otherwise identical to pPHP6265, was used as a negative control. For ligase assays, pPHP6265 was digested at a unique SphI site. The linear plasmid DNA was purified by phenol-chloroform extraction followed by ethanol precipitation and suspended in 10 mM Tris buffer (pH 8.0) plus 0.1 mM EDTA for further use.

DNA Ligase Assays:

Reactions mixtures (20 µl final volume) contained 2 µl each of the appropriate 10× reaction buffer (provided with the commercially provided ligase enzymes as described above) and plasmid DNA (0.1 µg–1.0 µg per reaction) and 10 units of DNA ligase. ATP (10 mM final concentration) was used as a co-factor for the viral as well as eukaryotic enzyme and NAD was used for the bacterial enzyme. After ligation at 17° C. for 15–30 min., the reaction product was purified using QIA Quick Purification Kit (Qiagen, Inc.). The purified DNA was suspended in TE8.0 and used directly for the coupled transcription-translation assays.

Coupled Transcription-Translation Assays:

Two different TnT kits were used for this assay, the Single Tube Protein (STP) kit from Novagen or the TnT kit from Promega. Both systems use SP6 polymerase for transcription from the plasmid DNA, and translation can be performed using either wheat germ extract or red blood cell extract. Briefly, 1–2 µl ligated, purified DNA is mixed with the STP reaction mixture (25 µl final volume) or TnT reaction mixture (50 µl final volume), and incubated for 60–90 min. at 30° C. The reaction was stopped by simply putting the tubes on ice.

Luciferase Assay:

The luciferase activity of the coupled transcription-translation reaction product was measured using a Flowtech luminometer essentially as described earlier (34–36). Briefly, 1–10 µl of the reaction mixture from above step was pipefted directly into a luminometer cuvette containing 200 µl of the reaction mixture (25 mM Tricine pH 7.8 containing 500 µg/ml BSA, 5 mM ATP, 15 mM $MgCl_2$) mixed gently and put in the luminometer. Luciferin solution (500, µM in an aliquot of 100 µl) was automatically dispensed into the cuvette. Ten seconds after addition of the substrate, the enzyme activity was automatically recorded as Relative Light Units. Reactions without any protein were used to measure background activity, which was always less than 200 RLU.

EXAMPLE 4

Figure 2:
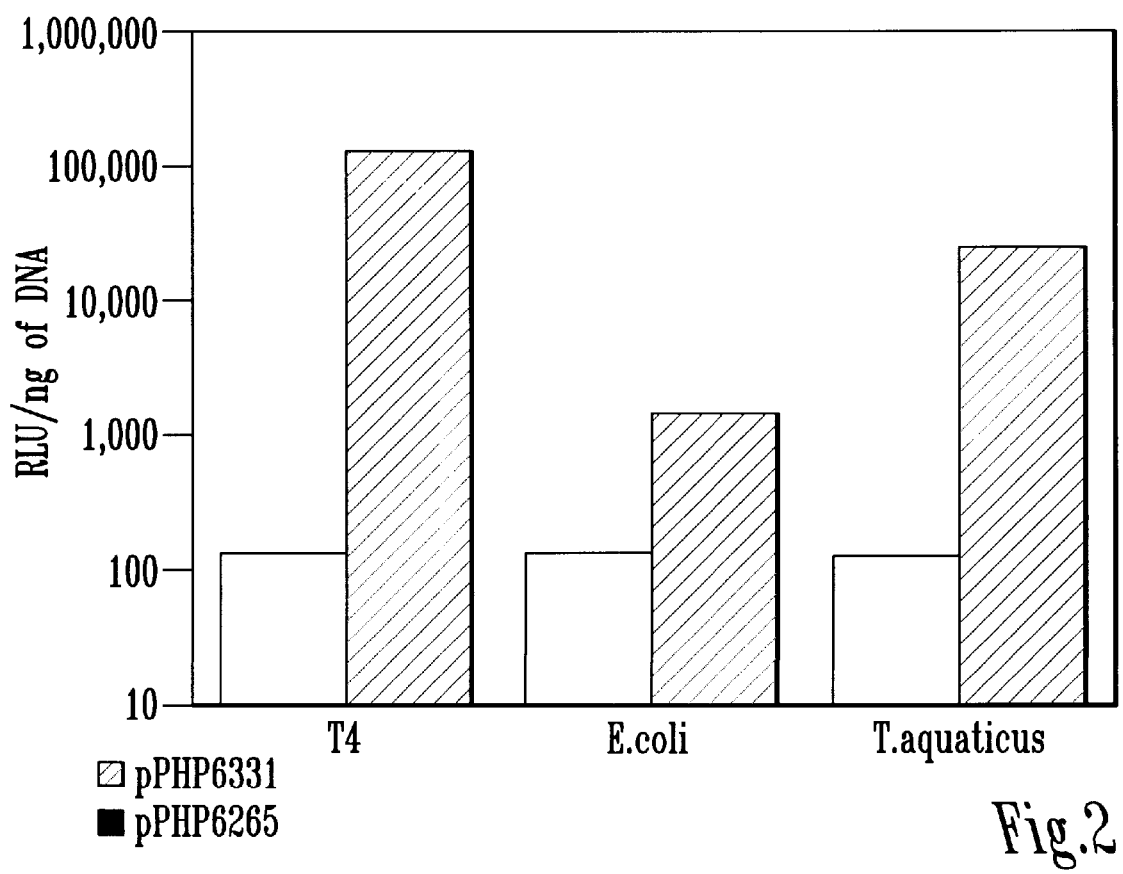
FIG. 2 shows the results of the DNA ligase assay of the invention as described in Example 2. Reactions were performed under conditions specific for T4, *E. coli*, or Tacquaticus enzymes, as appropriate. T4=2 Units; *E. coli* =10

Biological samples containing T4, *E. coli* and *T. aquaticus* DNA ligases were obtained commercially, as in Example 3. Using the protocol disclosed in Example 3, the pPHP6265 plasmid was constructed and prepared, and digested at a SphI site. Ligase reactions were performed under conditions specific for T4, *E. Coli*, or *T aquaticus* enzymes per manufacturers' specifications. The purified ligase reaction products were suspended in 50 µTE and 2 µl (approximately 40 ng) were used in each coupled transcription-translation reaction. Luciferase activity was measured in triplicate, and the results are shown in FIG. 2.

Although the foregoing invention has been described in some detail, for purposes of clarity of understanding, by way of illustration and example, it will be clear to those of skill in the art that certain changes and modifications may be practiced within the scope of the appended claims.

REFERENCES

1. Gellert, M. (1967) Formation of covalent circles of λDNA by *E. coli* extracts. *Proc. Natl. Acad. Sci. U.S.A.*, 57:148–155.
2. Weiss, B. and Richardson, C. C. (1967) Enzymatic breakage and joining of deoxyribonucleic acid. 1. Repair of single strand breaks in DNA by an enzyme system from *Escherichia coli* infected with $T_4$ bacteriophage. ibid., 1021–1028.
3. Olivera, B. M. and Lehman, I. R. (1967) ibid., pp 1425–1433.
4. Gefter, M. L.; Becker, A.; and Hurwitz, J. (1967) ibid., 58:240–247.
5. Cozzarelli, N. R.; Melechen, N. E.; Jovin, T. M.; and Kornberg, A. (1967) Polynucleotide cellulose as a substrate for polynucleotide ligase included by phage $T_4$ Biochem. Biopys. Res. Commun., 28:578–586.
6. Lehman, I. R. (1974) DNA Ligase: Structure, Mechanism, and Function. *Science* 186:790–797.
7. Engler, M. J. (1982) DNA Ligases. In "The Enzymes", Vol. XV (Ed. Paul D. Boyer, Academic Press, Inc. New York) pp. 3–29.
8. Higgins, N. P. and Cozzarelli, N. R. (1979) DNA joining enzymes: A review. *Methods Enzymol.*, 68:50–71.
9. Lasko, D. D.; Tomkinson, A. E.; and Lindahl, T. (1990), Eukaryotic DNA Ligases. *Mutation Res.*, 236:277–287.
10. Lindahl, T. and Barnes, D. E. (1992) Mammalian DNA ligases, *Ann. Rev. Biochem.*, 61:251–281.
11. Willis, A. E.; Lindahl, T. (1987) DNA ligase I deficiency in Bloom's syndrome. *Nature*, 325:355–357.
12. Chan, J. Y.; Becker, F. F.; German, J.; Ray, J. H. (1987) Altered DNA ligase I activity in Bloom's syndrome cells, *Nature*, 325:357–359.
13. Willis, A. E.; Weksberg, R.; Tomlinson, S.; Lindahl, T. (1987) Structural alterations of DNA ligase I in Bloom syndrome, *Proc. Nati. Acad. Sci. U.S.A.*, 84:8016–8020.
14. Runger, T. M.; Kraemer, K. H. (1989) Joining of linear plasmid DNA is reduced and error-prone in Bloom's syndrome cells. *EMBO J.* 8:1419–1425.
15. Lehmann, A. R.; Norris, P. G. (1990) DNA repair deficient photodermatoses, *Semin Dermatol*, 9:55–62.
16. Petrini, J. H.; Huwiler, K. G.; Weaver, D. T. (1991) A wild-type DNA ligase I gene is expressed in Bloom's syndrome cells, *Proc. Natl. Acad. Sci. U.S.A.*, 88:7615–7619.
17. Barnes, D. E.; Tomkinson, A. E.; Lehmann, A. R.; Webster, A. D.; Lindahl, T. (1992) Mutations in the DNA ligase I gene of an individual with immunodeficiencies and cellular hypersensitivity to DNA-damaging agents, *Cells*, 69:495–503.
18. Prigent, C.; Satoh, M. S.; Daly, G.; Barnes, D. E.; Lindahl, T. (1994) Aberrant DNA repair and DNA replication due to an inherited enzymatic defect in human DNA ligase 1, *Mol. Cell Biol.*, 14:310–317.
19. Kok, F.; Neumann, S.; Sarde, C. O.; Zheng, S.; Wu, K. H.; Wei, H. M.; Bergin, J.; Watkins, P. A.; Gould, S.; Sack, G., et al. (1995) Mutational analysis of patients with X-linked adrenoleukodystrophy, *Hum. Mutat.*, 6:104–115.
20. Maniatis, T.; Fritsch, E. E.; and Sambrook, J. (1989) Molecular Cloning-A laboratory manual, Cold Spring Harbor Laboratory, Cold Spring Harbor, N.Y.
21. Maunders, M. J. (1993) DNA and RNA ligases, *Methods Mol. Biol.*, 16:213–230.
22. Landegren, U.; Kaiser, R.; Sanders, J.; Hood, L. (1988) A ligase-mediated gene detection technique, *Science*, 241:1077–80.
23. Yamanishi, K.; Yasuno, H. (1993) Ligase chain reaction (LCR), *Hum. Cell*, 6:143–147.
24. Laffler, T. G.; Carrino, J. J.; Marshall, R. L. (1993) The ligase chain reaction in DNA-based diagnosis, *Ann. Biol. Clin.* (Paris), 51:821–826.
25. Kalin, I.; Shephard, S.; Candrain, U. (1992) Evaluation of the ligase chain reaction (LCR) for the detection of point mutations, *Mutat. Res.*, 283:119–123.
26. Abravaya, K.; Carrino, J. J.; Muldoon, S.; Lee, H. H. (1995) Detection of point mutations with a modified ligase chain reaction (Gap-LCR), *Nucleic Acids Res.*, 23:675–682.
27. Barker, D. G.; Johnson, A. L.; Johnson, L. H. (1985) An improved assay for DNA ligase reveals temperature-sensitive activity in cdc9 mutants of Saccharomyces cerevisiae, *Mol. Gen. Genet.*, 200:458–462.
28. Hansen, T. S.; Petersen, N. E.; litia, A.; Blaabjerg, O.; Hyltoft-Petersen, P.; Horder, M. (1995) Robust nonradioactive oligonucleotide ligation assay to detect a common point mutation in the CYP2D6 gene causing abnormal drug metabolism, *Clin. Chem.*, 41:413–418.
29. Eggerding, F. A.; lovannisci, D. M.; Brinson, E.; Grossman, P.; Winn-Deen, E.S. (1995) Fluorescencebased oligonucleotide ligation assay for analysis of cystic fibrosis transmembrane conductance regulator gene mutations, *Hum. Mutat.*, 5:153–165.
30. Konarska, M.; Filipowicz, W.; Domdey, H. and Gross, H. J. (1981) Formation of a 2'-phosphomonoester, 3', 5'-phosphodister linkage by a novel RNA ligase in wheat germ, *Nature*, 293:112–116.
31. Furneaux, H.; Pick, L. and Hurwitz, J. (1983) Isolation and characterization of RNA ligases from wheat germ, *Proc. Natl. Acad. Sci. U.S.A.*, 80:3933–3937.
32. Shuman, S.; Shurks, ;M.; Furneaux, H. and Hurwitz, J. (1980) Purification and characterization of a GTP pyrophosphate exchange activity from vaccinia virions, *J. Biol. Chem.*, 255:11588–11598.
33. Bradford, M. M. (1976) A rapid and sensitive method for the quantification of microgram quantities of protein utilizing the principle of protein-dye binding. *Anal. Biochem.*, 72:248–254.
34. Goodchild, J.; Vishwanatha, J. K. (1991) A novel assay for DNA ligase, *Nucleic Acids Res.*, 19:3745.
35. Unger, E.; Parsons, R. L.; Schmidt, R. J.; Bowen, B.; Roth, B. A. (1993) Dominant negative mutants of Opaque2 suppress transactivation of a 22-kD zein promoter by Opaque2 in maize endosperm cells, *Plant Cell*, 5:831–841.
36. Callis, J.; Fromm, M.; Walbot, V. (1987) Introns increase gene expression in cultured maize cells, *Genes Dev.*, 1:1183–1200.

What is claimed is:

1. A quantitative and functional method for detection of DNA ligase activity in a biological sample, the method comprising:

(a) preparing a plasmid containing an expressible reporter gene;

(b) preparing a biological sample to be assayed for DNA ligase activity;

(c) disrupting the plasmid containing an expressible reporter gene using one or more restriction enzymes;

(d) using the disrupted plasmid as a substrate for a ligation reaction run in the presence of the biological sample;

(e) partially purifying the ligation reaction DNA product (s) produced in step (d);

(f) subjecting the partially purified DNA products of the ligation reaction to a coupled transcription-translation reaction; and (g) quantifying the extent of ligation by measuring the activity of the coupled transcription-translation reaction product.

2. The method of claim 1 wherein the biological sample comprises an extract of prokaryotic cells.

3. The method of claim 1 wherein the biological sample comprises an extract of eukaryotic cells or tissues.

4. The method of claim 3 wherein the eukaryotic cells or tissues comprise plant cells or tissues.

5. The method of claim 1 wherein the biological sample comprises a mixture of expression products from a cDNA library.

6. The method of claim 1 wherein the reporter gene encodes a chemiluminescent product.

7. The method of claim 1 wherein the reporter gene encodes a fluorescent product.

8. The method of claim 1 wherein the reporter gene encodes a product detectable in a colorametric reaction.

9. The method of claim 1 wherein the plasmid is disrupted using a single restriction enzyme which truncates at the 3' end of the reporter gene.

10. The method of claim 1 further comprising decreasing the nuclease activity in the biological sample prior to the ligation reaction.

11. The method of claim 10 wherein the nuclease activity in the biological sample is decreased by a partial purification of the biological sample.

12. The method of claim 10 wherein the nuclease activity in the biological sample is decreased by addition of one or more chemical nuclease inhibitors.

* * * * *